United States Patent
Giselbrecht et al.

(10) Patent No.: US 6,395,903 B1
(45) Date of Patent: *May 28, 2002

(54) PROCESS FOR THE PREPARATION OF 2,3-PYRIDINEDICARBOXYLIC ACIDS

(75) Inventors: Karlheinz Giselbrecht, Pasching; Eduard Perndorfer, Traun; Klaus Reiter, Linz, all of (AT)

(73) Assignee: DSM Fine Chemicals Austria Nfg GmbH & CoKG, Linz (AT)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/569,057

(22) Filed: May 10, 2000

(30) Foreign Application Priority Data

May 10, 1999 (AT) .............................................. 832/99

(51) Int. Cl.$^7$ ............................................ C07D 213/80
(52) U.S. Cl. ...................................................... 546/321
(58) Field of Search .................................. 546/321, 299

(56) References Cited

FOREIGN PATENT DOCUMENTS

| | | | |
|---|---|---|---|
| GB | 880592 | * | 10/1961 |
| NL | 1006654 | | 7/1997 |

OTHER PUBLICATIONS

Chemical Abstract 118:6484 (1993).
Chemical Abstract 116:241645 (1992).
Chemical Abstract 112:198071 (1990).
Chemical Abstract 88:22560 (1978).
Chemical Abstract 68:83716 (1968).
Chemical Abstract 69:35876 (1968).
"Ozonolysis of Quinolines: A Versatile Synthesis of Polyfunctional Pyridines", Synthesis, pp. 880–882, vol. 11.*
O'Murchu et. al.,"Ozonolysis of quinolines: a versatile synthesis of polyfunctional pyridines", synthesis, pp. 880–882, vol. 11, 1989.*
O'Murchu et. al., "Ozonolysis of quinolines: a versatile Synthesis of polyfunctional pyridines", synthesis, pp. 880–882, vol. 11, 1989.*
Kalakutskii et al., "Preparation of quinolinic acid by the ozonolyis of quinoline", Zh. Prikl. Khim., pp. 2121–2122, vol. 50(9), 1989.*

* cited by examiner

Primary Examiner—Alan L. Rotman
Assistant Examiner—Binta Robinson
(74) Attorney, Agent, or Firm—Wenderoth, Lind & Ponack, LLP

(57) ABSTRACT

Process for the preparation of pure 2,3-pyridinedicarboxylic acids of the formula I

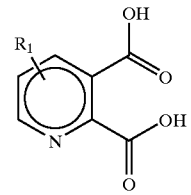

which are substituted in position 4 and/or 5 and/or 6 by $R_1$, where $R_1$ is hydrogen, $C_1-C_4$ alkyl, $C_1-C_4$ alkoxy, $C_1-C_4$ alkoxy-$C_1-C_4$ alkyl, halogen, hydroxyl or nitro, from quinolines of the formula II

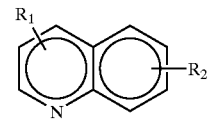

in which $R_1$ is as defined above, and which are substituted in position 6 and/or 7 by $R_2$, where $R_2$ is hydrogen, $C_1-C_4$ alkyl, $C_1-C_4$ alkoxy, $C_1-C_4$ alkoxy-$C_1-C_4$ alkyl, halogen, hydroxyl, nitro or amino, which are reacted in the first step in aqueous sulfuric acid or nitric acid solution with ozone in the ratio of from 1:2 to 1:3 at temperatures from 0 to +50° C., and the resulting peroxide solution is then reacted at temperatures of from +0 to +100° C. in the presence of 0.5–4.0 mol of oxidizing agent per mole of ozonolysis product formed, after which the pH of the reaction solution is adjusted to 0.2 to 3, the mixture is cooled to 0 to 30° C., and the precipitated pyridinedicarboxylic acid is isolated.

8 Claims, No Drawings

PROCESS FOR THE PREPARATION OF 2,3-PYRIDINEDICARBOXYLIC ACIDS 2,3-Pyridinedicarboxylic acids (PDCA) are an important raw material for the synthesis of pharmaceutical and agricultural chemicals.

Various processes for the preparation of PDCA are already known from the literature. Some are based on the oxidation of quinoline and some on the oxidation of quinoline derivatives which are substituted on the aromatic ring to impart activation.

The method, described firstly by Hoogewerff and van Dorp in Chem. Ber., page 425 et seq. (1883), of oxidizing quinoline from coal tar using potassium permanganate in an alkaline medium, however, produces only very low yields of PDCA, in addition to a large amount of byproducts.

The other processes for oxidizing quinoline are essentially derived from the method, described by Stix and Bulgatsch in Chem. Ber. Page 11 et seq. (1932), of oxidation using hydrogen peroxide in the presence of a copper salt. Since this reaction is extremely difficult to handle, several improvements have already been proposed which bring about better control of the reaction and a slight increase in the yield. Examples thereof are EP-A-0 024 197 or EP-A-0 034 943. In all of these variants, however, the copper salt of PDCA is always firstly formed, from which the free acid must be liberated using a sulfide. A further disadvantage is that complete removal of the copper ions is extremely difficult, meaning that PDCA prepared in this manner always contains traces of copper.

DE-A-31 50 005 describes a further oxidation process in which quinoline derivatives are oxidized with chlorate ions, vanadyl(V) cations being used as catalyst. However, this process is only suitable for quinoline derivatives in which at least one hydrogen atom in the benzene ring is replaced by an activating group, while the readily available and more cost-effective unsubstituted quinoline cannot be oxidized using this process.

Other oxidation processes, as described, for example, in DE-A-33 45 223, produce the desired end product PDCA only in low yields of about 52%.

Another method, the ozonolysis of quinoline or quinoline derivatives, for the preparation of pyridinedicarboxylic acids is described, for example, in U.S. Pat. No. 2,964,529. According to U.S. Pat. No. 2,964,529, benzazines from the group consisting of quinoline, isoquinoline and substituted quinolines and isoquinolines are reacted in the first step with ozone, preferably at temperatures of from 25 to 65° C. in the presence of at least one mole of mineral acid, preferably $HNO_3$, per mole of benzazine, and subsequently at elevated temperature with an oxidizing agent. As experimental values, or the color of the end products showed, the purity of the resulting pyridinedicarboxylic acids is, however, unsatisfactory. This is the case particularly when the starting material used is quinoline which has come directly from the distillation of coal tar and contains up to 5% of isoquinoline. Isoquinoline impurities are very troublesome in the preparation of 2,3-pyridinedicarboxylic acids since they form 3,4-pyridinedicarboxylic acids, which have correspondingly poorer solubility.

Accordingly, the object of the invention was to find an improved process for the preparation of 2,3-pyridinedicarboxylic acids in which, even in the presence of relatively large amounts of isoquinoline in the starting material, the desired 2,3-pyridinedicarboxylic acids are obtained in high yield and high purity.

The invention therefore provides a process for the preparation of pure 2,3-pyridinedicarboxylic acids of the formula I

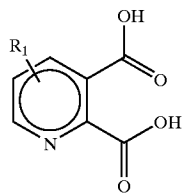

which are substituted in position 4 and/or 5 and/or 5 by $R_1$, where $R_1$ is hydrogen, $C_1$–$C_4$ alkyl, $C_1$–$C_4$ alkoxy, $C_1$–$C_4$ alkoxy-$C_1$–$C_4$ alkyl, halogen, hydroxyl or nitro, by ozonolysis in aqueous, mineral acid solution and subsequent oxidation in the presence of an oxidizing agent, which comprises reacting quinolines of the formula II

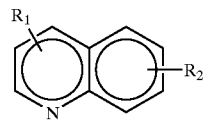

in which $R_1$ is as defined above, and which are substituted in position 6 and/or 7 by $R_2$, where $R_2$ is hydrogen, $C_1$–$C_4$ alkyl, $C_1$–$C_4$ alkoxy, $C_1$–$C_4$ alkoxy-$C_1$–$C_4$ alkyl, halogen, hydroxyl, nitro or amino, in the first step in aqueous sulfuric acid or nitric acid solution with ozone in the ratio of from 1:2 to 1:3 at temperatures from 0 to +50° C., and then reacting the resulting peroxide solution at temperatures of from +0 to +100° C. in the presence of 0.5–4.0 mol of oxidizing agent per mole of ozonolysis product formed, then adjusting the pH of the reaction solution to 0.2 to 3, cooling the mixture to 0 to 30° C., and isolating the precipitated pyridinedicarboxylic acid.

In the process according to the invention, 2,3-pyridinedicarboxylic acids of the formula I are prepared. The process starts from quinolines of the formula II which are substituted by the radicals $R_1$ and $R_2$. In the formula II, $R_1$ is in position 2 and/or 3 and/or 4 and is hydrogen, $C_1$–$C_4$ alkyl, $C_1$–$C_4$ alkoxy, $C_1$–$C_4$ alkoxy-$C_1$–$C_4$ alkyl, halogen, hydroxyl or nitro. Preferably, only one of positions 2, 3 or 4 is substituted by a radical $R_1$, which is not hydrogen. Particularly preferably, $R_1$ in position 2 and 4 is hydrogen, and in position 3 is methyl, ethyl or methoxymethyl. In addition, the quinolines of the formula II have, in position 6 and/or 7, the substituents $R_2$. $R_2$ is a group which is inert under the reaction conditions, such as hydrogen, $C_1$–$C_4$ alkyl, $C_1$–$C_4$ alkoxy, $C_1$–$C_4$ alkoxy-$C_1$–$C_4$ alkyl, halogen, hydroxyl, nitro or amino. $R_2$ is preferably hydrogen.

Particular preference is accordingly given to using an unsubstituted quinoline or a quinoline substituted in position 3 by methyl, ethyl or methoxymethyl. According to the invention, it is possible to use either pure quinoline, or quinoline which comes directly, i.e. without a purification step, from the distillation of coal tar and comprises up to 5% of isoquinoline.

The quinolines of the formula II are reacted according to the invention in aqueous sulfuric acid or nitric acid solution to give the corresponding 2,3-pyridinedicarboxylic acids. Preference is given to using sulfuric acid. In the process, enough acid is added to the reaction mixture for the pH of the reaction solution to be between 0.1 and 4, preferably between 0.3 and 1.5 and particularly preferably between 0.4 and 1. The concentration of starting material is preferably between 2 and 30% by weight, particularly preferably between 2.5 and 10% by weight.

The aqueous sulfuric acid or nitric acid quinoline solution is admixed with ozone in a quinoline: ozone ratio of from 1:2 to 1:3, preferably up to 1:2.5, particularly preferably up to 1:2.3. For this, an ozone-carrying stream of $O_2$ is passed into the reaction solution, preferably in a circulation apparatus or in a suitable batch apparatus, until the appropriate amount of ozone has been absorbed. The end of the reaction is achieved in most cases when the theoretical amount of ozone has been consumed. The end of the reaction is preferably determined by suitable in-process monitoring of the consumption of the quinoline.

The temperature during the ozonolysis is from 0 to +40° C., preferably 0 to 10° C. and particularly preferably 2 to 5° C.

In some instances, the addition of an ozone-stable antifoam to the ozonolysis solution can be advantageous. Preference is given to using antifoams based on silicone, the amount of antifoam added being dependent on the extent of the tendency toward foaming, and preferably being from about 0.01 to 0.2% by volume, particularly preferably from 0.05 to 0.15% by volume, based on the total amount of ozonolysis solution.

Following the ozonolysis step, the resulting peroxide solution is oxidized. For this, a suitable oxidizing agent is added to the peroxide solution. Suitable oxidizing agents are hydrogen peroxide, hypochlorite, peracids, peroxodisulfate, perborates, potassium permanganate etc. The oxidation can also be carried out catalytically with oxygen in the presence of transition metal catalysts. Preference is given to using hydrogen peroxide in the form of a 3 to 70% strength solution, particularly preferably as a 20 to 50% strength solution. The amount of oxidizing agent is between 0.5 and 4.0 mol per mole of ozonolysis product formed, or between 0.5 and 1.5 mol equivalents (mequ), preferably between 0.7 and 1.2, particularly preferably between 0.8 and 1 mequ of hydrogen peroxide (or of oxidizing agent), based on the quinoline used. The temperature during the oxidation is from 0 to +100° C., preferably between 10 and 70° C., particularly preferably between 15 and 50° C.

When the reaction is complete, i.e. after about 1 to 24 hours,, the resulting reaction mixture is treated with alkali until a pH between 0.2 and 3, preferably between 0.7 and 2 and particularly preferably between 0.9 and 1.1 is reached. For the alkali treatment, customary basic additives, such as, for example NaOH, KOH etc., are used. Preference is given to using NaOH or KOH, particularly preferably 40 to 50% strength NaOH. Simultaneously or subsequently the reaction mixture is cooled to from 0 to 30° C., preferably to from 4 to 10° C., as a result of which the corresponding 2,3-pyridinedicarboxylic acid crystallizes out.

To isolate the desired end product, the solid produced is filtered off with suction, removed by centrifugation or filtered off, washed, preferably with water and methanol, and subsequently dried. By working-up the mother liquor, e.g. by concentration by evaporation, the yield of desired end product can be increased by up to 10%.

The process according to the invention is therefore suitable for the preparation of 2,3-pyridinedicarboxylic acids of the formula I, in particular for the preparation of unsubstituted 2,3-pyridinedicarboxylic acids, or 2,3-pyridinedicarboxylic acids substituted in position 5 by methyl, ethyl or methoxymethyl, in high yields of greater than 80% having a content of more than 99.8%.

This is highly advantageous, particularly when quinoline which comes directly from the distillation of coal tar and comprises up to 5% of isoquinoline as impurity is used. Compared to the prior art, using the process according to the invention, even in the case of this contaminated starting material, gives essentially higher purities of the end product. This is of considerable importance in the further processing of the 2,3-pyridinedicarboxylic acids to give the corresponding pharmaceutical and agricultural chemicals.

Accordingly, the present invention further provides for the use of the 2,3-pyridinedicarboxylic acids prepared according to the invention for the preparation of pharmaceutical and agricultural chemicals, such as, for example, for the herbicides Arsenal, Cadre, Persuit, Imazamox etc., or for antimycobacterial quinolones.

EXAMPLE 1

140 g (1.08 mol) of quinoline 97.5%, Sumitomo, comprising 1.5% of isoquinoline, were dissolved in 1770 g of distilled water and 212.6 g of 98% strength sulfuric acid (2.16 mol), giving an approximately 7% strength solution having a pH of 0.3. An ozone-carrying stream of $O_2$ was passed through this solution at 6° C. in a circulation ozonization apparatus. The duration of the ozonolysis reaction was 8 h and 40 min, 118 g (2.46 mol) of ozone being consumed. Three drops of antifoam (Antifoam SRE, Wacker) diluted with 50 ml of water were added as required. A total of 17 ml of the antifoam solution were required.

When ozonolysis was complete, 2094 g of peroxide solution were obtained, to which 216 g (1.86 mol) of hydrogen peroxide (30% strength) were added with stirring in a reaction vessel precooled to 20° C. During the addition, the temperature increased to 24° C. The reaction mixture was stirred overnight and then, at a temperature between 20 and 30° C., 305 g of 40% strength NaOH were added, as a result of which the pH was adjusted from 0.3 to 1.0. The mixture was then cooled to 8° C., so that 2,3-pyridinedicarboxylic acid crystallized out. The solid formed was filtered off with suction, washed with water and methanol (2×100 ml) and dried.

Yield: 125 g (71.14%) having a content of 99.7% (GC+HPLC)

Following work-up of the mother liquor by concentration by evaporation, a further 5% of 2,3-pyridinedicarboxylic acid were obtained.

Analysis showed that the end product contained no 3,4-pyridinedicarboxylic acid impurity.

What is claimed is:

1. A process for the preparation of pure 2,3-pyridinedicarboxylic acids of the formula

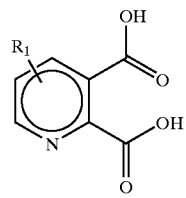

which is substituted in position 4 and/or 5 and/or 6 by $R_1$, where $R_1$ is hydrogen, $C_1$–$C_4$ alkyl, $C_1$–$C_4$ alkoxy, $C_1$–$C_4$ alkoxy-$C_1$–$C_4$ alkyl, halogen, hydroxyl or nitro, by ozonolysis in aqueous, mineral acid solution at 0 to 10° C. and subsequent oxidation in the presence of an oxidizing agent, which comprises reacting a quinoline of the formula

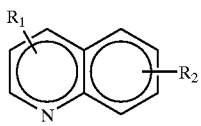

in which $R_1$ is as defined above, and which is substituted in position 6 and/or 7 by $R_2$, where $R_2$ is hydrogen, $C_1$–$C_4$ alkyl, $C_1$–$C_4$ alkoxy, $C_1$–$C_4$ alkoxy-$C_1$–$C_4$ alkyl, halogen, hydroxyl, nitro or amino, in a first step in aqueous sulfuric acid or nitric acid solution, having a pH between 0.3 and 1.5, with ozone in the ratio from 1:2 to 1:3 at temperatures from 0 to +10° C., and then reacting the resulting peroxide solution at temperatures of from +0 to +100° C. in the presence of 0.5–4.0 mol of oxidizing agent per mole of ozonolysis product formed, then adjusting the pH of the reaction solution to 0.7 to 2, cooling the mixture to 0 to 30° C., and isolating the precipitated pyridinedicarboxylic acid.

2. The process as claimed in claim 1, wherein the quinoline of the formula II used is a pure quinoline or a quinoline contaminated with up to 5% of isoquinoline.

3. The process as claimed in claim 1, wherein quinolines of the formula II in which $R_1$ in position 2 and 4 is hydrogen, and in position 3 is methyl, ethyl or methoxymethyl, and $R_2$ is hydrogen are used.

4. The process as claimed in claim 1, wherein 0.5 to 1.5 mol equivalents of oxidizing agent, based on the quinoline used, are used.

5. The process as claimed in claim 1, wherein the temperature during the oxidation is between 15 and 50° C.

6. The process as claimed in claim 1, wherein, following the oxidation, the pH of the reaction solution is adjusted to a value between 0.9 and 1.1.

7. The process as claimed in claim 1, wherein, to precipitate out the pyridinedicarboxylic acid, the reaction solution is cooled to a temperature between 4 and 10° C.

8. The process according to claim 1 wherein the quinoline starting material comes directly from the distillation of coal tar and contains up to 5% of isoquinoline.

* * * * *